United States Patent [19]

Dierdorf et al.

[11] Patent Number: 5,712,414
[45] Date of Patent: Jan. 27, 1998

[54] HYDROXYCARBOXYLIC ACID ANILIDES

[75] Inventors: Andreas Dierdorf; Theodor Papenfuhs, both of Frankfurt, Germany

[73] Assignee: Hoechst Aktiengesellschaft, Germany

[21] Appl. No.: 677,515

[22] Filed: Jul. 10, 1996

[30] Foreign Application Priority Data

Jul. 10, 1995 [DE] Germany .................. 195 25 098.2

[51] Int. Cl.[6] ................................................. C07C 231/02
[52] U.S. Cl. ........................... 564/138; 554/61; 554/62; 554/65; 558/418; 564/141; 564/420; 564/421; 564/422; 564/423
[58] Field of Search ..................... 564/138, 141, 564/420, 421, 422, 423; 554/61, 62, 65; 558/418

[56] References Cited

U.S. PATENT DOCUMENTS

| 2,604,481 | 7/1952 | Henry | 260/401 |
| 3,350,450 | 10/1967 | Dorell et al. | 260/577 |
| 3,538,162 | 11/1970 | Dorell | 260/576 |
| 4,286,105 | 8/1981 | Parker | 564/205 |
| 4,334,073 | 6/1982 | Diehr | 546/245 |
| 4,552,699 | 11/1985 | Mähnle et al. | 260/404.5 |

FOREIGN PATENT DOCUMENTS

| 0 221 494 | 5/1987 | European Pat. Off. |
| 0221449 | 2/1991 | European Pat. Off. |
| 0 678 502 | 10/1995 | European Pat. Off. |
| 0 695 738 | 2/1996 | European Pat. Off. |
| 2904490 | 8/1980 | Germany |
| 3 038 598 | 5/1982 | Germany |
| 3 244 956 | 6/1984 | Germany |
| 48-68503 | 9/1973 | Japan |
| 93/22278 | 11/1993 | WIPO |

OTHER PUBLICATIONS

Synthetic Communications, Bd. 23, Nr. 9, 1993; pp. 2761–2770; Branko S. Jursic et al: "A simple preparation of amides from acids and amines by heating of their mixture".

*Primary Examiner*—Peter O'Sullivan
*Attorney, Agent, or Firm*—Connolly and Hutz

[57] ABSTRACT

The present invention relates to a process for the preparation of hydroxycarboxylic acid amides of the general formula (1):

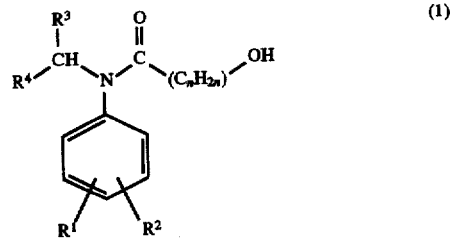

in which $R^1$ and $R^2$ are identical or different and are hydrogen, halogen, cyano, a linear or branched alkyl, alkenyl, alkynyl or alkoxy group having 1 to 12 carbon atoms, an aralkyl group having 7 to 12 carbon atoms, a cycloalkyl group having 6 to 12 carbon atoms or an aryl group having 6 to 12 carbon atoms, $R^3$ is hydrogen or a linear or branched alkyl group having 1 to 4 carbon atoms, $R^4$ is hydrogen or a linear or branched alkyl group having 1 to 6 carbon atoms, or $R^3$ and $R^4$, together with the carbon atom to which they are attached, form a five- or six-membered cycloalkane ring, and n is an integer from 1 to 12, wherein an aniline of the general formula (2)

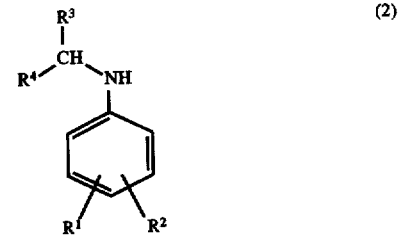

in which $R^1$, $R^2$, $R^3$ and $R^4$ are as defined in the formula (1), is reacted with a hydroxycarboxylic acid of the general formula (3)

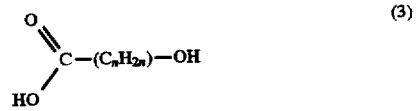

in which n is as defined in the formula (1), in the presence or absence of an inert solvent, at 150° to 250° C., and the constituents which are volatile under the reaction conditions are distilled out of the reaction mixture.

22 Claims, No Drawings

HYDROXYCARBOXYLIC ACID ANILIDES

The present invention relates to a novel process, representing an improvement compared with the state of the art, for the preparation of hydroxycarboxylic acid anilides from the corresponding N-alkylanilines.

Hydroxycarboxylic acid anilides, especially glycolic acid anilides, constitute a significant group of substances and are used as important precursors for the preparation of herbicides (EP-A-300 344) and pharmaceutical active substances (EP-A-284 338, EP-A-363 284) and for the preparation of fungicides (U.S. Pat. No. 4,440,780).

The importance of this group of substances is such that there has been no lack of attempts in the past to find different ways of obtaining hydroxycarboxylic acid amides and especially hydroxycarboxylic acid anilides.

Thus DE-OS-3 038 598 discloses a process for the preparation of α-hydroxycarboxylic acid amides wherein α-oxycarboxylic acid amides, especially the corresponding formyloxy compounds, are reacted with alcohols in the presence of catalytic amounts of alkali metal or alkaline earth metal hydroxides, hydrogen carbonates or carbonates. The corresponding α-hydroxycarboxylic acid amides are formed as a result of the transesterification which takes place in this reaction. As the α-oxycarboxylic acid amides required for the reaction have to be prepared in a separate step by reacting α-chlorocarboxylic acid amides with alkali metal formates, the preparation of the α-hydroxycarboxylic acid amides from the corresponding α-chlorocarboxylic acid amides is in reality a two-step process which additionally has the disadvantage that the preparation of the α-oxycarboxylic acid amides is carried out in the presence of a quaternary ammonium salt, such quaternary ammonium salts being known to cause problems when the effluent is treated.

Another process for the preparation of α-hydroxycarboxylic acid amides can be found in DE-OS-2 904 490 (U.S. Pat. No. 4,334,073). In a first step, α-halogenocarboxylic acid amides are reacted with an alkali metal or alkaline earth metal acetate in the presence of a quaternary ammonium salt and, if appropriate, with the use of a diluent, to give the corresponding α-acetoxycarboxylic acid amides, and the latter are deacylated by reaction with an alcohol in the presence of catalytic amounts of an alkali metal or alkaline earth metal hydroxide or an alkali metal or alkaline earth metal carbonate. This process is also a two-step process in which the use of quaternary ammonium salts again causes undesirable contamination of the effluent.

DE-OS-3 539 394 (EP-A-221 449) also relates to a two-step process for the preparation of glycolic acid amides, chloroacetamides being reacted with potassium carbonate, in the presence of an aprotic amide as diluent and, if appropriate, in the presence of a phase transfer catalyst, to give symmetrical carbonates, and the latter being deacylated by means of a transesterification reaction with a primary alcohol, in the presence of an alkali metal hydroxide, either in a separate second step after prior isolation, or directly without intermediate isolation. In all the Examples, however, the reaction is carried out in the presence of a phase transfer catalyst. Moreover, the sometimes very low yields (22 to 80%) leave something to be desired.

The processes described above are relatively expensive because they provide the desired hydroxycarboxylic acid amides via two separate reaction steps taking place in succession. In addition, the quaternary ammonium salts used as phase transfer catalysts cause problems in terms of the waste products obtained in the course of the reaction. They are undesirable especially because of their unfavorable properties in the effluent. Furthermore, chlorine-containing carboxylic acid amides are used as starting materials, but the use of chlorine-containing substances is problematic for reasons of environmental pollution and because of their corrosive properties.

In Synthetic Communications, 23 (19), 2761 to 2770 (1993), Jurišić and Zdravskovski describe the preparation of carboxylic acid amides by heating a mixture of a primary amine and a carboxylic acid according to the following equation:

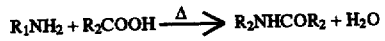

$$R_1NH_2 + R_2COOH \xrightarrow{\Delta} R_2NHCOR_2 + H_2O$$

Temperatures of 160° to 180° C. and very short reaction times of only 10 to 30 minutes are given as optimum reaction conditions. It is expressly indicated that prolonged reaction times can cause the formation of appreciable amounts of tar.

The process relates only to the reaction of primary amines with carboxylic acids. Chloroform is added to the reaction mixture obtained, while hot, and extraction is carried out with water, aqueous potassium hydroxide and/or aqueous hydrochloric acid. After evaporation of the solvent, the product is recrystallized from carbon tetrachloride, chloroform/petroleum ether or petroleum ether (see page 2763).

This process has the disadvantages that, on the one hand, it is restricted to the use of primary amines and, on the other hand, only relatively short reaction times are permissible because of the expected formation of undesirable waste products in the form of thick oil and tar, it being necessary to ensure that a sufficient reaction does actually take place within these short reaction times. A further disadvantage is the labor-intensive working-up of the reaction mixture, coupled with the fact that a chlorine-containing solvent has to be used.

Considering the importance of hydroxycarboxylic acid anilides, it is a worthwhile object to provide a process for the preparation of hydroxycarboxylic acid anilides which avoids the disadvantages of the processes mentioned above, can be carried out in a simple manner using readily available starting materials and auxiliary substances, and also reduces the amount of waste products.

This object is achieved by a process for the preparation of hydroxycarboxylic acid amides of the general formula (1)

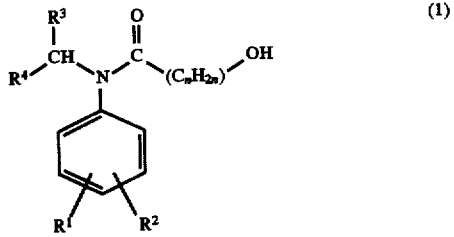

in which $R^1$ and $R^2$ are identical or different and are hydrogen, halogen, cyano, a linear or branched alkyl, alkenyl, alkynyl or alkoxy group having 1 to 12 carbon atoms, an aralkyl group having 7 to 12 carbon atoms, a cycloalkyl group having 6 to 12 carbon atoms or an aryl group having 6 to 12 carbon atoms, $R^3$ is hydrogen or a linear or branched alkyl group having 1 to 4 carbon atoms, $R^4$ is hydrogen or a linear or branched alkyl group having 1 to 6 carbon atoms, or $R^3$ and $R^4$, together with the carbon atom to which they are attached, form a five- or six-membered cycloalkane ring, and n is an integer from 1 to 12. In said process, an aniline of the general formula (2)

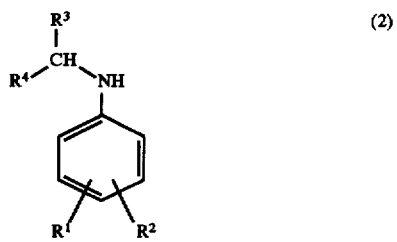

in which $R^1$, $R^2$, $R^3$ and $R^4$ are as defined in the formula (1), is reacted with a hydroxycarboxylic acid of the general formula (3)

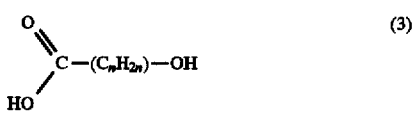

in which n is as defined in the formula (1), in the presence or absence of an inert solvent, at 150° to 250° C., and the constituents which are volatile under the reaction conditions are distilled out of the reaction mixture.

The process according to the invention has several advantages. On the one hand it produces the desired hydroxycarboxylic acid anilide in a single reaction step, and on the other hand it makes it possible to dispense both with the use of phase transfer catalysts and with ingredients containing a reactive chlorine atom, i.e. α-chlorocarboxylic acid amides or chlorine-containing solvents. The process according to the invention can be carried out without great technical expense and using readily available starting materials.

In view of the procedure described in Synthetic Communications, 23 (19), 2761 to 2770 (1993), where exclusively primary amines are used, it is surprising that anilines of the formula (2) containing a secondary amino group can be reacted with a hydroxycarboxylic acid of the formula (3). It was particularly unexpected that the anilines of the formula (2), whose structure is sterically generally bulkier than that of primary amines, could be reacted at all, and furthermore that the desired reaction products could be obtained in good yield and purity despite comparatively very long reaction times.

The reaction proceeds according to the following equation:

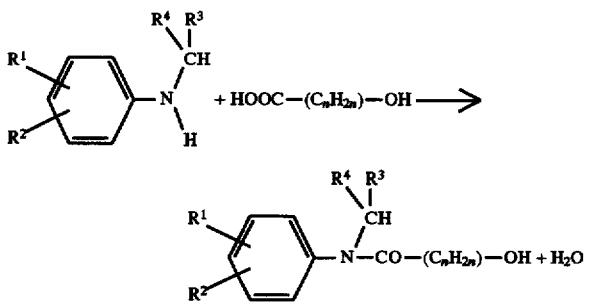

Anilines of the formula (2) which can successfully be used are those in which $R^1$ and $R^2$ are identical or different and are hydrogen, fluorine, chlorine, bromine or an alkyl or alkoxy group having 1 to 4 carbon atoms, especially those in which $R^1$ and $R^2$ are identical or different and are hydrogen, fluorine, chlorine, bromine or an alkyl group having 1 to 4 carbon atoms, and preferably those in which $R^1$ and $R^2$ are different and $R^1$ or $R^2$ is hydrogen.

It is recommended to use an aniline of the formula (2) in which $R^3$ is an alkyl group having 1 or 2 carbon atoms and $R^4$ is a linear or branched alkyl group having 1 to 4 carbon atoms, or $R^3$ and $R^4$, together with the carbon atom to which they are attached, form a cyclopentyl or cyclohexyl group, especially an aniline of the formula (2) in which $R^3$ is a methyl group and $R^4$ is a linear alkyl group having 1 to 4 carbon atoms, or $R^3$ and $R^4$, together with the carbon atom to which they are attached, form a cyclohexyl group, and preferably an aniline of the formula (2) in which $R^3$ and $R^4$ are a methyl group or, together with the carbon atom to which they are attached, form a cyclohexyl group.

The anilines of the formula (2) required for the process according to the invention can be prepared at comparatively low cost by reacting a nitrobenzene of the formula (4)

in which $R^1$ and $R^2$ are as defined in the aniline of the formula (2), and a carbonyl compound $R^3$—CO—$R^4$, in which $R^3$ and $R^4$ are as defined in the aniline of the formula (2), with hydrogen in the presence of a hydrogenation catalyst. Suitable hydrogenation catalysts are conventional catalysts containing nickel, cobalt, platinum or palladium, especially supported catalysts containing nickel, cobalt, platinum or palladium, the supports used being aluminum oxide, pumice, clay, $SiO_2$, kieselguhr, silicic acid, activated charcoal or mixtures thereof. It is also possible, however, to use unsupported catalysts, for example Raney nickel, Raney cobalt, platinum or palladium in metallic form.

The above reaction is described in greater detail in U.S. Pat. No. 3,350,450, for example using halogen-substituted aromatic nitro compounds in the presence of metal sulfide catalysts containing palladium, platinum, rhodium, ruthenium and cobalt as metals. Sulfited noble metal catalysts, especially sulfited platinum on activated charcoal, have also proved suitable for a number of such reactions (EP-0 479 877 B1).

A further advantage of the process according to the invention is that a reaction mixture is used which contains the aniline of the formula (2) and which is prepared by reacting a nitrobenzene of the formula (4)

in which $R^1$ and $R^2$ are as defined in the formula (2), and a carbonyl compound $R^3$—CO—$R^4$, in which $R^3$ and $R^4$ are as defined in the formula (2) with the exception of hydrogen, with hydrogen in the presence of a hydrogenation catalyst, but in the absence of an additional solvent.

This dispenses with the need for a separate working-up of the mixture obtained in this reaction; in particular, it is not necessary for the aniline of the formula (2) formed to be separated from the reaction mixture and reacted in pure form with the hydroxycarboxylic acid of the formula (3). The reaction mixture can be used directly in the process according to the invention, if appropriate after the hydrogenation catalyst has been separated off and if appropriate after water has been separated off.

This ensures a very simple procedure which starts from nitrobenzenes of the formula (4) and carbonyl compounds R³—CO—R⁴, in which R³ and R⁴ are as defined in the formula (2) with the exception of hydrogen, and which does not involve the high cost of a separate working-up or purification of the aniline of the formula (2).

As previously mentioned, this represents a further advantage of the process according to the invention.

Without implying a limitation, the following may be mentioned as examples of suitable anilines of the formula (2): N-alkyl-2-methoxyanilines, N-alkyl-4-methoxyanilines, N-alkyl-3,5-dimethylanilines, N-alkyl-2-chloroanilines, N-alkyl-4-chloroanilines, N-alkylanilines and N-alkyl-4-fluoroanilines, in which alkyl is a methyl, ethyl, propyl, isopropyl, butyl, 2-butyl or 2-pentyl group or a substituted or unsubstituted cyclopentyl or cyclohexyl group.

As mentioned at the outset, a hydroxycarboxylic acid of the formula (3), $HOOC(C_nH_{2n})OH$, is used, especially a hydroxycarboxylic acid of the formula $HOOC(CH_2)_nOH$, i.e. one in which the —$(C_nH_{2n})$— group is a —$(CH_2)_n$— group.

As already mentioned at the outset, in the formula (3) relating to the hydroxycarboxylic acid, n is an integer from 1 to 12, especially an integer from 1 to 4 and preferably 1.

The process according to the invention can be carried out in the presence or absence of an inert solvent, an inert solvent being understood as meaning a solvent which does not react under the reaction conditions, i.e. behaves as inert.

If an inert solvent is used, it should have a sufficiently high boiling point. Without implying a limitation, suitable inert solvents which may be mentioned here are mesitylene, decalin, N-methylpyrrolidone, N,N-dimethylacetamide and N,N-diethylacetamide. It is also possible to use mixtures of inert solvents. The process is particularly simple to carry out if an inert solvent is dispensed with, an option which has no disadvantages in many cases.

As already mentioned previously, the reaction is carried out at 150° to 250° C. In a large number of cases, it has proved satisfactory to carry out the reaction at 160° to 220° and especially 170° to 190° C.

The aniline of the formula (2) and the hydroxycarboxylic acid of the formula (3) are conventionally used in a molar ratio of 15:1 to 1:15, especially 10:1 to 1:10, preferably 5:1 to 1:5 and particularly preferably (4 to 5):1. It is frequently sufficient to use both starting materials in the stoichiometric ratio or one of the two starting materials in an excess of up to 300 and especially 200 mol %.

The constituents which are volatile under the reaction conditions are removed from the reaction mixture by distillation. This can be done before the reaction has started, for example during heating, volatile constituents being removed from the ingredients. It is also possible to perform this distillation at a later stage, when the reaction is in progress. However, as well as volatile constituents which accompany the ingredients, it is always necessary to remove volatile constituents which are formed during the reaction, especially the water of reaction.

The volatile constituents can be distilled off continuously or batchwise.

It is particularly advantageous if the constituents which are volatile under the reaction conditions are distilled out of the reaction mixture during the reaction. Volatile constituents which are distilled off are water and, if appropriate, cleavage products formed during the reaction, unreacted aniline of the formula (2), unreacted nitrobenzene of the formula (4), unreacted carbonyl compound and reaction products thereof.

The volatile constituents can be distilled off under reduced pressure, atmospheric pressure or superatmospheric pressure.

Independently of the distillation, the process according to the invention can be carried out under reduced pressure, atmospheric pressure or superatmospheric pressure.

In a particularly simple embodiment, the process according to the invention is carried out under atmospheric pressure.

It can be carried out either continuously or batchwise, a batchwise procedure being particularly simple.

The Examples which follow describe the invention in greater detail without implying a limitation.

EXPERIMENTAL SECTION

EXAMPLE 1 a) Preparation of N-isopropyl-4-fluoroaniline 564.5 g (4 mol) of 4-fluoronitrobenzene, 255.6 g (4.4 mol) of acetone and 8 g of a platinum catalyst on activated charcoal (sulfited; 50% moisture content) are placed in an autoclave (volume: 2 liters) fitted with a reciprocating stirrer, and are reacted at 80° to 90° C. under a hydrogen pressure of 6 to 10 bar, with stirring. When the uptake of hydrogen has ceased, the mixture is cooled, the autoclave is depressurized and the catalyst is filtered off.

This gives 812 g of a reaction mixture composed of an aqueous phase and an organic phase. The aqueous phase is separated off in a separating funnel.

The organic phase (589.2 g) contains 97.4% of N-isopropyl-4-fluoroaniline, as determined by gas chromatography, corresponding to a theoretical yield of 94%.

b) Preparation of Glycolic Acid N-isopropyl-(4-fluoroanilide) without a Solvent In a glass flask (volume: 250 ml) fitted with a stirrer, 157 g (1 mol) of the crude N-isopropyl-4-fluoroaniline obtained from Example 1a) (97.4% pure) and 19 g (0.25 mol) of glycolic acid are heated at 180° C. for 21 hours, with stirring. The constituents which are volatile under the reaction conditions, especially the water of reaction formed, are distilled off during the reaction. When the reaction is complete, excess N-isopropyl-4-fluoroaniline is separated off by distillation and the glycolic acid N-isopropyl-(4-fluoroanilide) formed is purified by fractional distillation.

The yield is 71.9%, based on the glycolic acid used, and the purity of the glycolic acid N-isopropyl-(4-fluoroanilide) obtained by fractional distillation is 98.7%, as determined by gas chromatography.

EXAMPLE 2 a) Preparation of N-sec-butyl-4-methylaniline 411 g (3 mol) of 4-nitrobenzene, 238 g (3.3 mol) of butan-2-one and 8 g of a platinum catalyst on activated charcoal (sulfited; 50% moisture content) are placed in an autoclave (volume: 2 liters) fitted with a reciprocating stirrer, and are reacted at 100° C. under a hydrogen pressure of 10 bar, with stirring. When the uptake of hydrogen has ceased (after a reaction time of 5.5 hours), the mixture is cooled, the autoclave is depressurized and the catalyst is filtered off.

This gives 698 g of a reaction mixture composed of an aqueous phase and an organic phase. The aqueous phase is separated off in a separating funnel.

The organic phase contains 21.5% of 4-methylaniline and 76.7% of N-sec-butyl-4-methylaniline, as determined by gas chromatography.

The 4-methylaniline is distilled off to give 266 g of a crude product containing 98.3% of N-sec-butyl-4-methylaniline (as determined by gas chromatography).

b) Preparation of Glycolic Acid N-sec-butyl-(4-methylanilide) without the Addition of a Solvent In a glass flask (volume: 250 ml) fitted with a stirrer, 163 g (1 mol) of the crude N-sec-butyl-4-methylaniline obtained from Example 2a) and 15.2 g (0.2 mol) of glycolic acid are heated at 188° C. for 7 hours, with stirring. The constituents which are volatile under the reaction conditions, especially the water of reaction formed, are distilled off during the reaction. When the reaction is complete, excess N-sec-butyl-4-methylaniline is separated off by distillation and the glycolic acid N-sec-butyl-(4-methylanilide) formed is purified by fractional distillation. The glycolic acid N-sec-butyl-(4-methylanilide) distils at 148° to 154° C. (4 mbar). The yield is 50%, based on the glycolic acid used, and the purity of the glycolic acid N-sec-butyl-(4-methylanilide) obtained by fractional distillation is 99.7%, as determined by gas chromatography.

Analytical data: Melting point: 46°–47° C. $^1$H NMR (300 MHz, $d_6$-DMSO): $\delta$=0.89 (t, 3H), 0.98 (d, 2H), 1.23 (sept, 1H), 1.41 (sept, 1H), 2.34 (s, 3H), 3.52 (d, 2H), 4.31 (t, 1H), 4.57 (m, 1H), 7.09 (d, 2H), 7.25 (d, 2H); IR (capillary): 3440, 3050, 2980, 2940, 2880, 1770, 1650, 1620, 1520, 830 cm$^{-1}$; MS (70 eV): m/z=221 (M$^+$), 192, 165, 134 (100%), 91, 57.

EXAMPLE 3 a) Preparation of N-sec-butyl-4-ethoxyaniline 501 g (3 mol) of 4-ethoxynitrobenzene, 238 g (3.3 mol) of butan-2-one and 8 g of a platinum catalyst on activated charcoal (sulfited; 50% moisture content) are placed in an autoclave (volume: 2 liters) fitted with a reciprocating stirrer, and are reacted at 100° C. under a hydrogen pressure of 10 bar, with stirring. When the uptake of hydrogen has ceased, the mixture is cooled, the autoclave is depressurized and the catalyst is filtered off.

This gives 729.5 g of a reaction mixture composed of an aqueous phase and an organic phase. The aqueous phase is separated off in a separating funnel.

The organic phase (577.4 g) contains 0.78% of 4-ethoxyaniline, 94% of N-sec-butyl-4-ethoxyaniline and 3.8% of 4-ethoxynitrobenzene, as determined by gas chromatography.

The 4-ethoxyaniline is distilled off to give 475 g of a crude product containing 97.7% of N-sec-butyl-4-ethoxyaniline (as determined by gas chromatography).

b) Preparation of Glycolic Acid N-sec-butyl-(4-ethoxyanilide) without the Addition of a Solvent In a glass flask (volume: 500 ml) fitted with a stirrer, 197.5 g (1 mol) of the crude N-sec-butyl-4-ethoxyaniline obtained from Example 3a) and 15.2 g (0.2 mol) of glycolic acid are heated at 180° C. for 8 hours, with stirring. The constituents which are volatile under the reaction conditions, especially the water of reaction formed, are distilled off during the reaction.

When the reaction is complete, excess N-sec-butyl-4-ethoxyaniline is separated off by distillation and the glycolic acid N-sec-butyl-(4-ethoxyanilide) formed is purified by fractional distillation. The glycolic acid N-sec-butyl-(4-ethoxyanilide) distils at 170° C. (5.3 mbar).

The yield is 33.3% (16.6 g), based on the glycolic acid used, and the purity of the glycolic acid N-sec-butyl-(4-ethoxyanilide) obtained by fractional distillation is 99.5%, as determined by gas chromatography.

Analytical data: Melting point: 62.5° C. $^1$H NMR (300 MHz, $d_6$-DMSO): $\delta$=0.88 (t, 3H), 0.96 (d, 3H), 1.31 (m, 2H), 1.33 (t, 3H), 3.51 (d, 2H), 4.04 (q, 2H), 4.36 (t, 1H), 4.57 (m, 1H), 6.97 (d, 2H), 7.12 (d, 2H); IR (KBr): 3410, 3080, 2985, 2940, 1650, 1520, 1250, 590 cm$^{-1}$; MS (70 eV): m/z=251 (M$^+$), 222, 195, 164 (100%), 136, 108, 41.

EXAMPLE 4

Preparation of Glycolic Acid N-methylanilide (Starting from Pure N-methylaniline)

In a glass flask (volume: 100 ml) fitted with a stirrer, 42.8 g (0.4 mol) of N-methylaniline and 7.6 g (0.1 mol) of glycolic acid are heated at 180° C. for 3.75 hours, with stirring. The constituents which are volatile under the reaction conditions, especially the water of reaction formed, are distilled off during the reaction.

When the reaction is complete, the reaction mixture obtained (46 g) is fractionally distilled under reduced pressure (2.7 mbar) to give the following fractions:

Fraction 1: 21.1 g (97.5% of N-methylaniline; 0.19% of glycolic acid N-methylanilide)

Fraction 2: 5.8 g (98.1% of N-methylaniline; 0.77% of glycolic acid N-methylanilide)

Fraction 3: 1.6 g (60.0% of N-methylaniline; 35.9% of glycolic acid N-methylanilide)

Fraction 4: 11.0 g (3.2% of N-methylaniline, 95.4% of glycolic acid N-methylanilide)

Fraction 4 (melting point: 41.5° to 46.5° C.), weighing 11.0 g, corresponds to a yield of 66.7%, based on the glycolic acid used.

EXAMPLE 5

Preparation of Glycolic Acid N-methylanilide (Starting from Pure N-methylaniline and Aqueous Glycolic Acid)

In a glass flask (volume: 250 ml) fitted with a stirrer, 85.6 g (0.8 mol) of N-methylaniline and 26.7 g of 57% aqueous glycolic acid solution (corresponding to 0.2 mol of glycolic acid) are heated at 175° C. for 4 hours, with stirring. The constituents which are volatile under the reaction conditions, especially the water used as solvent for the glycolic acid and the water of reaction formed, are distilled off during the reaction.

When the reaction is complete, the reaction mixture obtained is distilled under reduced pressure (2.6 mbar) to give the following fractions:

Fraction 1: 64 g (91.5% of N-methylaniline; 1.6% of glycolic acid N-methylanilide)

Fraction 2: 23 g (0.2% of N-methylaniline; 97.2% of glycolic acid N-methylanilide)

Fraction 2 (melting point: 49° to 51.5° C.), weighing 23.0 g, corresponds to a yield of 69.7%, based on the glycolic acid used.

We claim:

1. A process for the preparation of hydroxycarboxylic acid amides of the general formula (1):

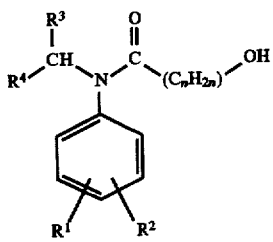  (1)

in which $R^1$ and $R^2$ are identical or different and are hydrogen, halogen, cyano, a linear or branched alkyl, alkenyl, alkynyl or alkoxy group having 1 to 12 carbon atoms, an aralkyl group having 7 to 12 carbon atoms, a cycloalkyl group having 6 to 12 carbon atoms or an aryl group having 6 to 12 carbon atoms, $R^3$ is hydrogen or a linear or branched alkyl group having 1 to 4 carbon atoms, $R^4$ is hydrogen or a linear or branched alkyl group having 1 to 6 carbon atoms, or $R^3$ and $R^4$, together with the carbon atom to which they are attached, form a five- or six-membered cycloalkane ring, and n is an integer from 1 to 12, which comprises reacting an aniline of the general formula (2)

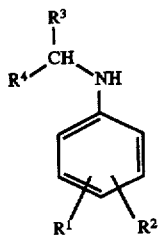  (2)

in which $R^1$, $R^2$, $R^3$ and $R^4$ are as defined in the formula (1), is reacted with a hydroxycarboxylic acid of the general formula (3):

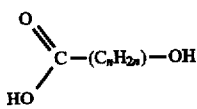  (3)

in which n is as defined in the formula (1), optionally in the presence of an inert solvent, at 150° to 250° C., and the constituents which are volatile under the reaction conditions are distilled out of the reaction mixture.

2. The process as claimed in claim 1, wherein an aniline of the formula (2) is used in which $R^1$ and $R^2$ are identical or different and are hydrogen, fluorine, chlorine, bromine or an alkyl or alkoxy group having 1 to 4 carbon atoms.

3. The process as claimed in claim 1 or 2, wherein an aniline of the formula (2) is used in which $R^1$ and $R^2$ are identical or different and are hydrogen, fluorine, chlorine, bromine or an alkyl group having 1 to 4 carbon atoms.

4. The process as claimed in claim 1, wherein an aniline of the formula (2) is used in which $R^1$ and $R^2$ are different and $R^1$ or $R^2$ is hydrogen.

5. The process as claimed in claim 1, wherein an aniline of the formula (2) is used in which $R^3$ is an alkyl group having 1 or 2 carbon atoms and $R^4$ is a linear or branched alkyl group having 1 to 4 carbon atoms, or $R^3$ and $R^4$, together with the carbon atom to which they are attached, form a cyclopentyl or cyclohexyl group.

6. The process as claimed in claim 1, wherein an aniline of the formula (2) is used in which $R^3$ is a methyl group and $R^4$ is a linear alkyl group having 1 to 4 carbon atoms, or $R^3$ and $R^4$, together with the carbon atom to which they are attached, form a cyclohexyl group.

7. The process as claimed in claim 1, wherein an aniline of the formula (2) is used in which $R^3$ and $R^4$ are a methyl group or, together with the carbon atom to which they are attached, form a cyclohexyl group.

8. The process as claimed in claim 1, wherein a reaction mixture is used which contains the aniline of the formula (2) and which is prepared by reacting a nitrobenzene of the formula (4)

  (4)

in which $R^1$ and $R^2$ are as defined in the formula (2), and a carbonyl compound $R^3$—CO—$R^4$, in which $R^3$ and $R^4$ are as defined in the formula (2) with the exception of hydrogen, with hydrogen in the presence of a hydrogenation catalyst, but in the essential absence of an additional solvent.

9. The process as claimed in claim 1, wherein a hydroxycarboxylic acid of the formula (3) is used in which the —$(C_nH_{2n})$— group is a —$(CH_2)_n$— group.

10. The process as claimed in claim 1, wherein a hydroxycarboxylic acid of the formula (3) is used in which n is an integer from 1 to 4.

11. The process as claimed in claim 1, wherein a hydroxycarboxylic acid of the formula (3) is used in which n is 1.

12. The process as claimed in claim 1, wherein mesitylene, decalin, N-methylpyrrolidone or N,N-dimethylacetamide is added as an inert solvent.

13. The process as claimed in claim 1, wherein the reaction is carried out at 160° to 220° C.

14. The process as claimed in claim 1, wherein the reaction is carried out at 170° to 190° C.

15. The process as claimed in claim 1, wherein the aniline of the formula (2) and the hydroxycarboxylic acid of the formula (3) are used in a molar ratio of 15:1 to 1:15.

16. The process as claimed in claim 1, wherein the aniline of the formula (2) and the hydroxycarboxylic acid of the formula (3) are used in a molar ratio of 10:1 to 1:10.

17. The process as claimed in claim 1, wherein the aniline of the formula (2) and the hydroxycarboxylic acid are used in a molar ratio of 5:1 to 1:5.

18. The process as claimed in claim 1, wherein the constituents which are volatile under the reaction conditions are distilled out of the reaction mixture during the reaction.

19. The process as claimed in claim 1, wherein water and, if appropriate, cleavage products formed during the reaction, unreacted aniline of the formula (2), unreacted nitrobenzene of the formula (4), unreacted carbonyl compound $R^3$—CO—$R^4$ and reaction products thereof are distilled off as volatile constituents.

20. The process as claimed in claim 1, wherein the volatile constituents are distilled off under reduced pressure.

21. The process as claimed in claim 1 wherein the volatile constituents are distilled off under atmospheric pressure.

22. The process as claimed in claim 1 wherein the volatile constituents are distilled off under superatmospheric pressure.

* * * * *